(12) United States Patent
Davies, Jr. et al.

(10) Patent No.: US 9,114,236 B2
(45) Date of Patent: Aug. 25, 2015

(54) NON-COMPLIANT MEDICAL BALLOON HAVING BRAIDED OR KNITTED REINFORCEMENT

(75) Inventors: William F. Davies, Jr., Athens, TX (US); Lanny R. Pepper, Larue, TX (US); Kelli L. Hayes, Athens, TX (US)

(73) Assignee: BARD PERIPHERAL VASCULAR, INC., Tempe, AZ (US)

( * ) Notice: Subject to any disclaimer, the term of this patent is extended or adjusted under 35 U.S.C. 154(b) by 206 days.

(21) Appl. No.: 13/567,533

(22) Filed: Aug. 6, 2012

(65) Prior Publication Data

US 2012/0296363 A1    Nov. 22, 2012

Related U.S. Application Data

(63) Continuation of application No. 13/072,861, filed on Mar. 28, 2011, now Pat. No. 8,715,229, which is a continuation of application No. 11/690,735, filed on Mar. 23, 2007, now Pat. No. 7,914,487, which is a continuation-in-part of application No. 10/967,038, filed on Oct. 15, 2004, now Pat. No. 7,354,419, and a continuation-in-part of application No. 10/967,065, filed on Oct. 15, 2004, now Pat. No. 7,682,335, and a continuation-in-part of application No. 10/966,970, filed on Oct. 15, 2004, now Pat. No. 7,309,324.

(60) Provisional application No. 60/785,864, filed on Mar. 24, 2006.

(51) Int. Cl.
*A61M 29/00* (2006.01)
*A61M 31/00* (2006.01)
*A61M 37/00* (2006.01)
*A61M 25/10* (2013.01)

(52) U.S. Cl.
CPC ......... *A61M 25/104* (2013.01); *A61M 25/1029* (2013.01); *A61M 2025/1075* (2013.01); *A61M 2025/1084* (2013.01); *A61M 2025/1086* (2013.01); *Y10T 29/49826* (2015.01)

(58) Field of Classification Search
CPC ..................... A61M 2025/1084; A61M 25/10; A61M 2025/1075; A61M 2025/1086; A61M 25/0012; A61M 25/0043; A61M 25/0045; A61M 25/005
USPC ................... 604/509, 96.01, 101.01–101.05, 604/102.01, 103, 103.05, 103.06, 912, 915
See application file for complete search history.

(56) References Cited

U.S. PATENT DOCUMENTS

| | | | |
|---|---|---|---|
| 5,891,114 A | 4/1999 | Chien et al. | |
| 6,213,995 B1 * | 4/2001 | Steen et al. | 604/527 |
| 7,252,650 B1 * | 8/2007 | Andrews et al. | 604/103.06 |
| 2004/0109964 A1 * | 6/2004 | Beckham | 428/35.9 |

* cited by examiner

Primary Examiner — Rebecca E Eisenberg
(74) Attorney, Agent, or Firm — King & Schickli, PLLC

(57) ABSTRACT

A non-compliant medical balloon comprises a base balloon including a pair of spaced-apart, generally conical end sections and a generally cylindrical center section connected therebetween. A braided fabric sleeve surrounds at least a portion of the base balloon, wherein the sleeve is formed of at least three substantially inelastic fibers intertwined in such a way that no two of the three fibers are twisted exclusively around one another. The sleeve is permanently affixed to the outer surface of the base balloon so as to prevent excessive expansion of the base balloon when the base balloon is internally pressurized.

7 Claims, 7 Drawing Sheets

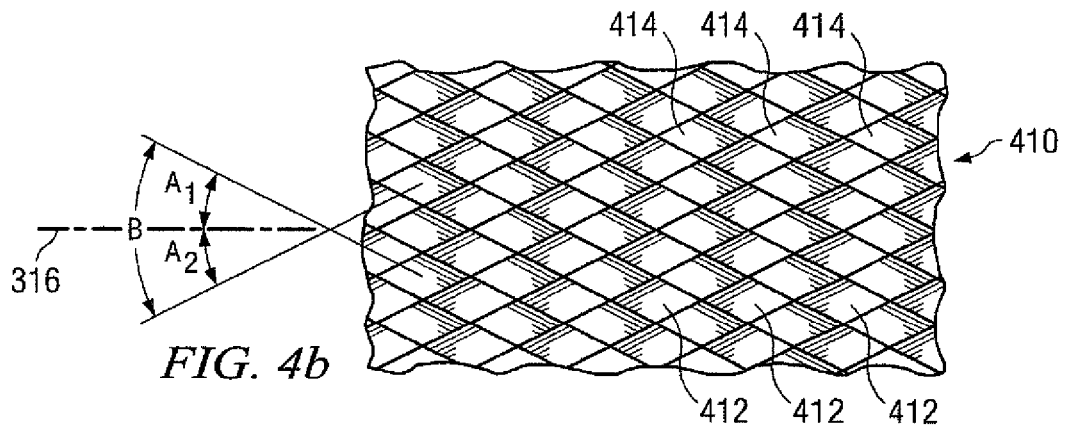
FIG. 4b
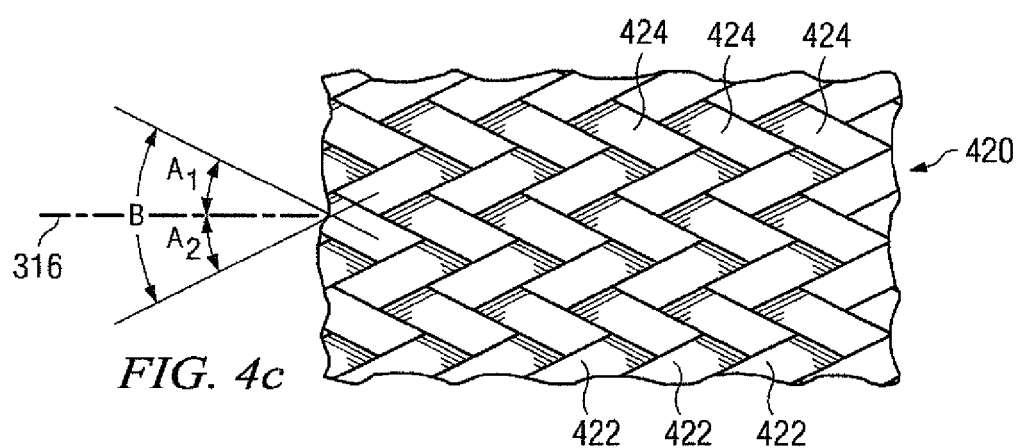
FIG. 4c
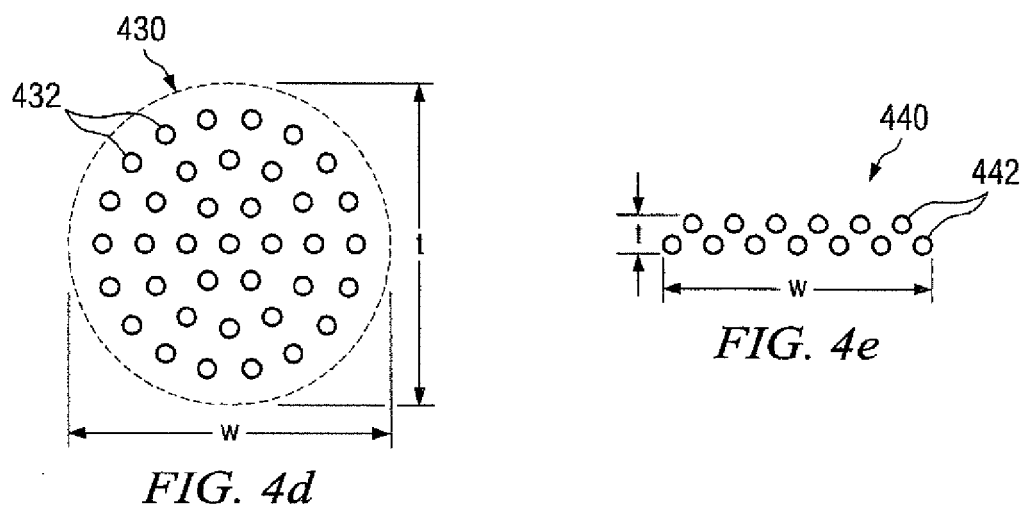
FIG. 4d
FIG. 4e

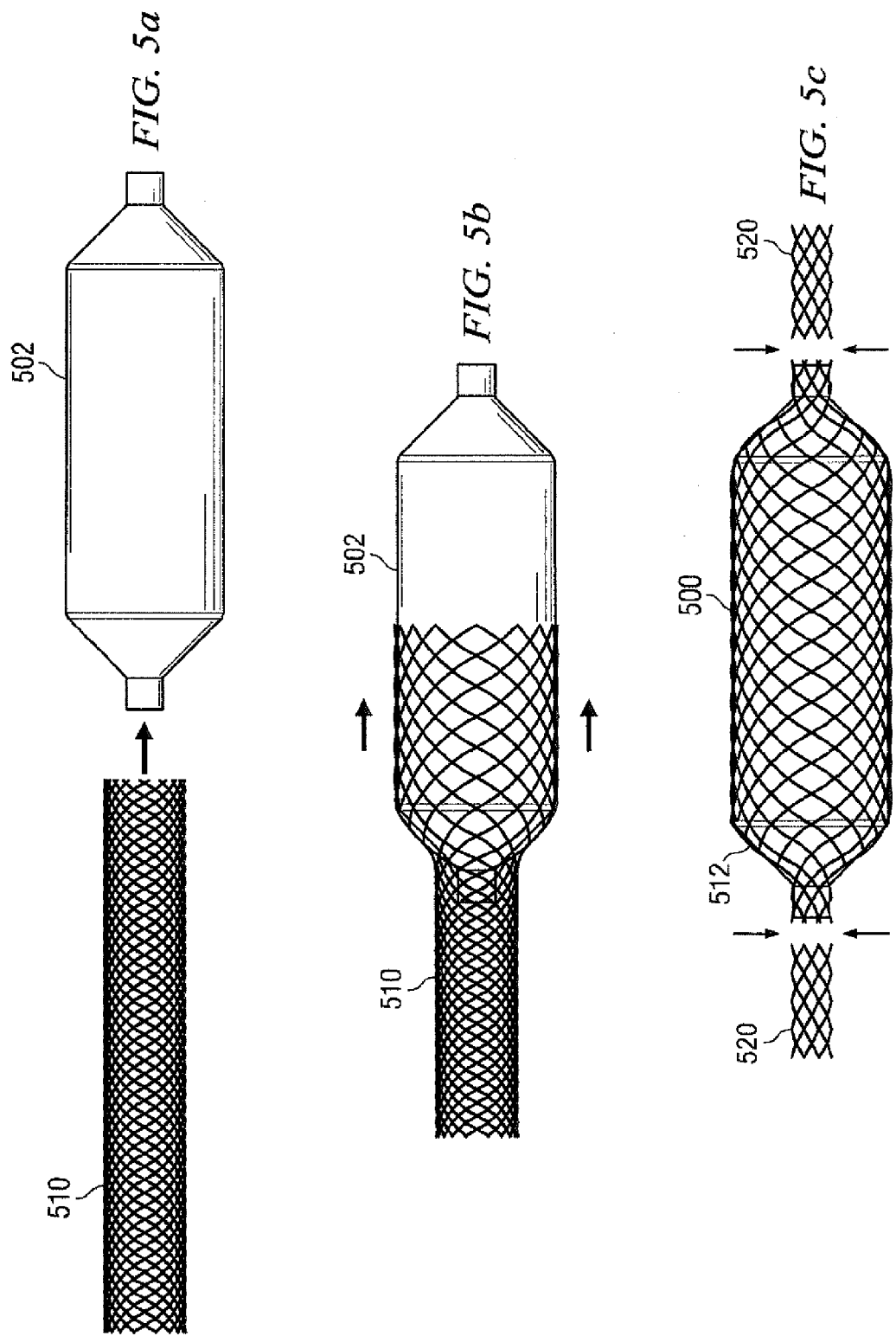

NON-COMPLIANT MEDICAL BALLOON HAVING BRAIDED OR KNITTED REINFORCEMENT

RELATED APPLICATION

This application is a continuation of U.S. Pat. application Ser. No. 13/072,861 filed Feb. 28, 2011 now U.S. Pat. No. 8,715,299, which is a continuation of U.S. Pat. application Ser. No. 11/690,735, filed Feb. 23, 2007, now U.S. Pat. No. 7,914,487 which is a continuation-in-part of U.S. application Ser. No. 10/967,038, filed Oct. 15, 2004, now U.S. Pat. No. 7,354,419 and entitled MEDICAL BALLOON HAVING STRENGTHENING RODS; a continuation-in-part of U.S. application Ser. No. 10/967,065, filed Oct. 15, 2004, now U.S. Pat. No. 7,682,335 and entitled NON-COMPLIANT MEDICAL BALLOON HAVING AN INTEGRAL NON-WOVEN FABRIC LAYER; and a continuation-in-part of U.S. application Ser. No. 10/966,970, filed Oct. 15, 2004, now U.S. Pat. No. 7,309,324 and entitled NON-COMPLIANT MEDICAL BALLOON HAVING AN INTEGRAL WOVEN FABRIC LAYER, the disclosures of which are incorporated herein by reference for all purposes. This application also claims the benefit of U.S. Provisional Application for Patent Ser. No. 60/785,864, filed Mar. 24, 2006, and entitled NON-COMPLIANT MEDICAL BALLOON HAVING BRAIDED REINFORCEMENT.

TECHNICAL FIELD

The following disclosure relates to medical balloons, and more particularly to non-compliant medical balloons used with a balloon catheter in medical procedures such as angioplasty.

BACKGROUND

Medical balloons have been widely used in medical procedures. Typically, an uninflated medical balloon is inserted into a body-space, e.g., blood vessel, urological vessel, etc. by means of a catheter. After positioning at the desired location within the body, the medical balloon is inflated by introducing a fluid into the balloon through the catheter under pressure. The inflation fluid causes the volume of the medical balloon to expand, and the adjacent body-space is similarly expanded. In procedures such as angioplasty, the inflated medical balloon may be used to open a collapsed or blocked artery. The fluid may then be withdrawn from the balloon, causing it to collapse to facilitate its removal from the body.

It is known to use medical balloons made of non-compliant materials for procedures where the dimensions of the inflated medical balloon must be uniform and predictable, even when different inflation pressures are used. Because the maximum diameter of such non-compliant balloons is predetermined, they are less likely to rupture or dissect the vessel or body-space when the balloon expands.

Before inflation, non-compliant medical balloons are typically folded tightly against the catheter in order to reduce the assembly's overall cross-section (i.e., to better fit through small body-spaces). It is thus normally desirable that the walls of the balloon be as thin as possible, so that the uninflated balloon will have the smallest diameter possible. However, medical balloons are increasingly being used to open body spaces restricted by tough tissues such as strictures, scarring or calcified areas. Stretching such tough tissue often requires the medical balloon to exert significant pressure. It is thus desirable that a medical balloon be capable of withstanding high pressure without rupturing. The pressure at which the walls of the balloon are expected to rupture is termed the "burst strength."

In the pursuit of non-compliant medical balloons having both thin walls and high burst strength, it is known to make so-called "composite" balloons from a blow-molded thin film polymeric material having externally applied fiber-reinforcements. In some cases, such reinforcing fibers may be "filament wound" around the blow-molded "base" balloon in a simple helical fashion. In other cases, successive layers of fibers may be laid over the base balloon in adjacent, but separate (i.e., not woven together) layers having different orientations. While such fiber-reinforced balloons have resulted in improved performance compared to non-reinforced balloons, further improvement is desired. A non-compliant medical balloon having an integral non-woven fabric layer is disclosed in co-pending U.S. patent application Ser. No. 10/967,065 entitled "Non-Compliant Medical Balloon Having an Integral Non-Woven Fabric Layer," filed Oct. 15, 2004, the disclosure of which is incorporated herein by reference for all purposes. A non-compliant medical balloon having an integral woven fabric layer is disclosed in co-pending U.S. patent application Ser. No. 10/966,970 entitled "Non-Compliant Medical Balloon Having an Integral Woven Fabric Layer," filed Oct. 15, 2004, the disclosure of which is incorporated herein by reference for all purposes. A medical balloon having strengthening rods is disclosed in co-pending U.S. patent application Ser. No. 10/967,038 entitled "Medical Balloon having Strengthening Rods," filed Oct. 15, 2004, the disclosure of which is incorporated herein by reference for all purposes.

"Braiding" refers to a system of fiber architecture in which three or more fibers are intertwined in such a way that no two fibers are twisted exclusively around one another. Braiding can be used to form fabric structures such as sheets, tapes, and even tubular sleeves having a continuous annular wall with a passage down the middle. The braided architecture resembles a hybrid of filament winding and weaving: As in filament winding, a tubular braid features seamless fiber continuity from end to end of a part; braided fibers are mechanically interlocked with one another. The resulting braid exhibits unique properties allowing it to be highly efficient in distributing loads. Specifically, because all the fibers within a braided structure are continuous and mechanically locked, a braid has a natural mechanism that evenly distributes load throughout the structure.

"Knitting" refers to a system of fiber architecture produced by intertwining threads in a series of interconnected loops rather than by weaving. In this fashion, the loops of fibers are mechanically interlocked. A weft-knitted structure consists of horizontal, parallel courses of fibers and requires only a single fiber. Alternatively, warp knitting requires one fiber for every stitch in the course, or horizontal row; these fibers make vertical parallel wales. Circular knitting refers to construction of a seamless tube whereas flat knitting is used to construct a flat structure.

The use of braided reinforcements for compliant medical balloons has been suggested. U.S. Pat. No. 5,647,848 to Jorgensen discloses a compliant medical balloon including an elastomeric balloon and a reinforcing structure that may include braided fibers. However, in such compliant balloons, the braid length and/or braid angle of the braided fiber structure changes between the deflated and inflated states, a condition that may be undesirable for non-compliant balloons.

A need therefore exists for a non-compliant medical balloon having braided fiber reinforcement. Preferably, the non-compliant braided fiber reinforced balloon will have a braid angle that does not change significantly between the deflated and inflated states.

A need further exists for a non-complaint medical balloon having knitted fiber reinforcement. Preferably, the non-compliant knitted fiber reinforced balloon will have knitted fibers that do not significantly change position relative to the surface of the base balloon between the deflated and inflated state.

SUMMARY

In one aspect thereof, a non-compliant medical balloon includes a base balloon having a pair of spaced-apart, generally conical end sections and a generally cylindrical center section connected therebetween. A braided fabric sleeve surrounds at least a portion of the base balloon, wherein the portion has at least two different diameters, and wherein the sleeve is formed of at least three substantially inelastic fibers intertwined in such a way that no two of the three fibers are twisted exclusively around one another. The sleeve is permanently affixed to the outer surface of the base balloon so as to prevent excessive expansion of the base balloon when the base balloon is internally pressurized.

In one configuration, a non-compliant medical balloon includes a base balloon including a generally cylindrical center section with first and second generally conical end portions extending from the center portion and having shoulders at the junctures of the conical end portions and the cylindrical center section. First and second reduced diameter necks extend from the apex of each of the conical end portions. A fabric sleeve is disposed over the base balloon, the sleeve being formed from mechanically interlocked, substantially inelastic fibers. The fibers are mechanically interconnected at spaced apart junctions where a fiber passes over an interconnecting fiber and changes direction until reaching the next junction. The sleeve extends continuously over the first conical end portion, the generally cylindrical center portion and the second conical end portion.

The fabric sleeve may be formed as a separate freestanding article that is subsequently pulled over the base balloon. Alternatively, the fabric sleeve may be formed in-situ over the base balloon. In one variation, the sleeve is formed from substantially inelastic ribbon-shaped fibers each having a width greater than thickness.

In one aspect, the sleeve of non-compliant medical balloon is braided from at least three substantially inelastic fibers intertwined so that no two of the three fibers are twisted exclusively around one another. In another, the fabric sleeve comprises a seamless tube extending continuously over the base balloon from the first neck to the second neck. Each fiber may be secured to the base balloon along substantially the entire length of the fiber to the base balloon.

In another aspect, the non-compliant medical balloon further includes an outer layer wherein the fabric sleeve is positioned between the base balloon and the outer layer and wherein the outer layer is secured to the base balloon with an adhesive or, alternatively, fused to the base balloon, such that the position of the fibers relative to the surface of base balloon does not substantially change when the balloon is inflated. In one aspect, a higher-strength adhesive is used to affix the reinforcing fibers to the base balloon at the conical end sections while a lower strength adhesive is used to secure the fibers to the remainder of the base balloon.

In another variation, the fabric sleeve is formed from substantially inelastic fibers that extend in a substantially longitudinal direction between the necks while changing directions at spaced apart intervals with substantially no fibers extending completely around the circumference of the base balloon. Alternatively, the fabric sleeve is formed from substantially inelastic fibers that extend in a substantially circumferential direction around the base balloon while changing directions at spaced apart intervals with substantially no fibers extending continuously between the necks in a longitudinal direction.

In another aspect, at least some of the mechanically interlocked, substantially inelastic fibers extend over the shoulders of the base balloon at an angle relative to the longitudinal axis of the cylindrical center portion and at an angle relative to a plane intersecting a circle defined by each shoulder such that transverse and longitudinal components of forces applied to the base balloon are transmitted across the shoulders.

In another aspect, a method of making a non-compliant medical balloon includes forming a base balloon having a generally cylindrical center section with first and second generally conical end portions extending from the center portion and with shoulders at the junctures of the conical end portions and the cylindrical center section. First and second reduced diameter necks are formed extending from the apex of each of the conical end portions. A fabric sleeve is formed from mechanically interlocked, substantially inelastic fibers, the fibers being mechanically interconnected at spaced apart junctions where a fiber passes over an interconnecting fiber and then changes direction such that the fiber intersects the junction at a first angle and extends away from the junction at a second angle. The fabric sleeve is positioned over the base balloon such that the fabric sleeve conforms to the surface of the base balloon and extends continuously over the base balloon between the first and second necks. The fabric sleeve is secured to the base balloon such that an angle between a longitudinal axis of the base balloon and fibers extending over the shoulders of the balloon does not change when the balloon is inflated or collapsed. In one variation, an overcoat is formed over the fabric sleeve such that the fabric sleeve is secured between the overcoat and the base balloon. In another, fabric sleeve is formed in-situ over the base balloon. The fabric sleeve may be one of knitted and braided construction.

BRIEF DESCRIPTION OF THE DRAWINGS

For a more complete understanding, reference is now made to the following description taken in conjunction with the accompanying drawings in which:

FIG. 4*b* is an enlarged portion of another medical balloon having an alternative braid variation;

FIG. 4*c* is an enlarged portion of yet another medical balloon having a further alternative braid variation;

FIG. 4*d* is a cross-sectional end view of a fiber bundle used in the FIG. 4*b*;

FIG. 4*e* is a cross-sectional end view of an alternative fiber bundle;

FIGS. 5*a*-5*d* show a method of making a non-compliant medical balloon having a braided fiber reinforcement layer in accordance with another embodiment;

DETAILED DESCRIPTION

Figure 1:
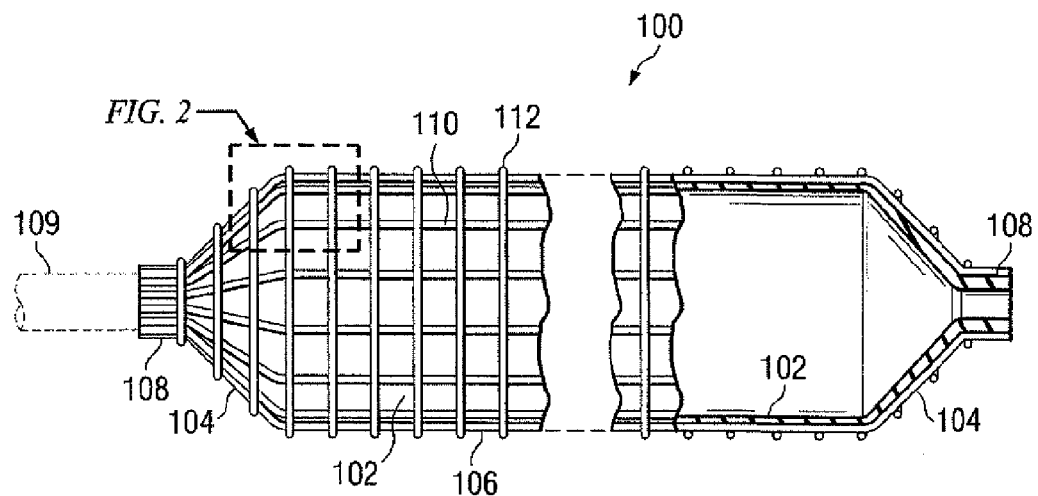
FIG. 1 is a partial cross-sectional side view of a medical balloon in accordance with the PRIOR ART.

Referring now to the drawings, wherein like reference numbers are used herein to designate like elements throughout the various views, embodiments of the non-compliant medical balloon are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated a non-compliant medical balloon in accordance with the prior art, in its inflated configuration. The medical balloon 100 includes a base balloon 102 having pairs of conical end sections 104 and a relatively cylindrical center-section 106 located therebetween. A small-diameter cylindrical neck 108 typically extends outwardly from each end section 106. For use, the balloon 100 is typically attached to a catheter 109 (shown in phantom) via the neck section 108. The base balloon 102 is commonly formed using a blow-molding process, resulting in the wall thickness of the end sections tapering considerably from the relatively thick neck 108 to the relatively thin center section 106. Fiber reinforcements may be applied to the outer surface of the base balloon 102, including a first layer of longitudinal fibers 110 oriented generally along the longitudinal axis of the balloon and a second layer of hoop fibers 112 oriented generally perpendicular to the longitudinal fibers, i.e., circumferentially around the axis of the balloon. It will be understood that the reinforcing fibers 110 and 112 are typically attached to the base balloon 102 using an adhesive material.

Figure 2:
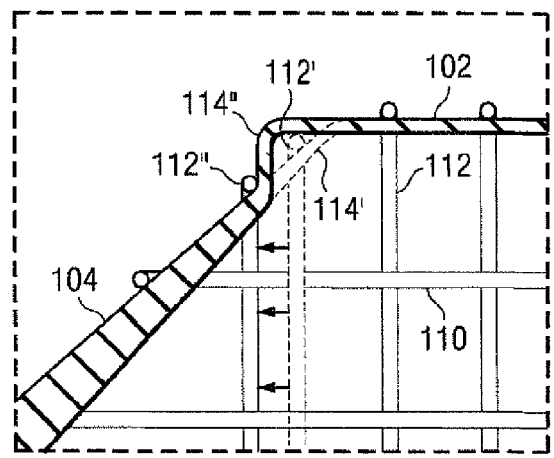
FIG. 2 is an enlarged cross-sectional view of the side junction region of the PRIOR ART medical balloon of FIG. 1.

Referring now to FIG. 2, there is illustrated an enlarged portion of the prior art balloon of FIG. 1, showing the balloon wall at the junction between the conical end section 104 and the center section 106. For purposes of illustration, the balloon in FIG. 2 is shown in cross section with the reinforcing fibers 110 and 112 (which are attached to the outer surface of the base balloon) visible through the transparent rear surface of base balloon 102. A recurring problem with such prior art balloons is failure of the adhesive bond on the sloped end sections 104, which allows the hoop fibers 112 on the end sections 104 to move during inflation, e.g., from their original position 112' (indicated in broken line) to a new position 112" further down the conical slope (as indicated by the small arrows). Once the hoop fibers 112 move out of position, the (now un-reinforced) corner section of the base balloon 102 may bulge out from its original position 114' (indicated in broken line) to a distended position 114" and fail due to pressure-induced strain (i.e., thinning). Such failures may include rupture of the balloon and release of pressurized inflation fluid into the patient.

Figure 3A:
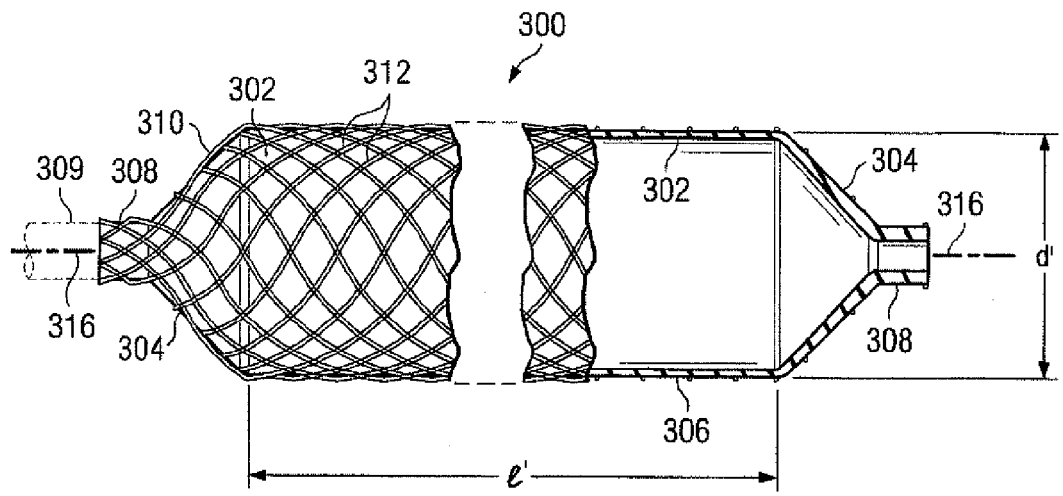
FIG. 3*a* is a partial cross-sectional side view of a non-compliant medical balloon having braided fiber reinforcement in accordance with one embodiment of the disclosure.

Referring now to FIG. 3a, there is illustrated a non-compliant medical balloon 300 having a braided fiber reinforcement layer in accordance with the disclosure. As in the prior art balloon 100 of FIG. 1, the medical balloon 300 may include a base balloon or balloon base layer 302 having a pair of conical end sections 304 and a relatively cylindrical center-section 306 located therebetween. A small-diameter cylindrical neck 308 may extend outwardly from each end section 306 for attachment to a catheter 309 (shown in phantom). The base balloon 302 may be formed of a thin film polymer material using a blow-molding process, resulting in the wall thickness of the end sections tapering considerably from relatively thick at the neck 308 to relatively thin at the center section 306. As in the prior art, fiber reinforcements are applied to the outer surface of the base balloon 302, however, in this embodiment, the fiber reinforcement layer comprises at least one single layer 310 of braided fibers 312 which are attached to the base balloon 302 when in its inflated configuration. The braided fiber reinforcement layer 310 may include three or more fibers 312 intertwined in such a way that no two fibers are twisted exclusively around one another. Braided fiber reinforcement layer 310 may comprise a seamless tube or may be constructed from a braided reinforcement fabric having one or more seams.

In some embodiments, the braided fiber reinforcement layer may be the only reinforcement layer. In other embodiments, additional fiber reinforcement layers of conventional longitudinal or circumferential configuration may be used in addition to the braided fiber layer. These conventional layers may be affixed to the balloon before and/or after the braided fiber layer.

For purposes of illustration, the braid form shown on the braided fiber reinforcement layer 310 of FIG. 3a has a very high "porosity," i.e., a relatively large amount of open space between braid fibers 312. It will be appreciated, however, that other braid forms having different patterns and porosities (including those having adjacent fibers with essentially no porosity) may be used in other embodiments. It will also be appreciated that different braid architectures may be used for the braided fiber reinforcement layer 310, including biaxial, triaxial and tailored braid forms.

In one embodiment, braided fiber reinforcement layer 310 has a braid density of from about 20 to about 60 pics per inch. In a preferred embodiment, braided fiber reinforcement layer 310 has a braid density from about 30 to about 50 pics per inch. In another variation, braided reinforcement layer 310 is formed with a braid density of about 45 to about 50 pics per inch.

The diameter d' of an inflated fiber-reinforced medical balloon 300 in accordance with the one embodiment may be about ten millimeters. In other variations, balloons 300 may have a diameter d' of about three millimeters to about thirty millimeters. The working length l' of an inflated fiber-reinforced medical balloon 300 in accordance with one embodiment may be about eight centimeters. In other variations, the working length l' of balloons 300 may vary from about one and one-half centimeters to about 15 centimeters. In various embodiments, the inclination angle of the conical end portion 304 of balloon 300 may vary from about twelve degrees to about twenty degrees. It will be recognized by those having skill in the art that the fiber-reinforced balloon 300 could be made in a wide variety of diameters d' and lengths l' and with a variety of inclinations at the conical end portions 304 of the balloon.

Fiber-reinforced balloon 300 is generally suitable for use as a medical balloon. Medical balloons are commonly used in angioplasty, orthopaedics and other medical procedures where it is necessary to create a space within the body. It may be recognized by those skilled in the art that the qualities of a fiber-reinforced balloon 300 may make the balloon 300 suitable for other uses. The fiber-reinforced balloons 300 may be used non-medically to create space or otherwise. The fiber-reinforced balloons 300 may be used in ways beyond the present uses of medical balloons.

The base layer balloon 302 is typically formed of a thin film polymeric material, or other suitable materials with high strength relative to film thickness. Polymers and copolymers that can be used for the base balloon 302 include the conventional polymers and copolymers used in medical balloon construction, such as, but not limited to, polyethylene, PET, polycaprolactam, polyesters, polyethers, polyamides, polyurethanes, polyimides, ABS, nylons, copolymers, polyester/polyether block copolymers, ionomer resins, liquid crystal polymers, and rigid rod polymers. The base layer balloon 302 may typically be formed as a blow-molded balloon of highly oriented polyethylene terephthalate (PET).

The strength of fiber-reinforced balloons 300 permits the use of base layer balloons 302 having a wall thickness less than conventional or prior art balloons without sacrifice of burst strength, abrasion resistance, or puncture resistance. The wall thickness of base layer balloon 302 may be in the range of about 0.0005 inch to about 0.002 inch. In accordance with the disclosed embodiment, the base layer balloon 302 may have a wall thickness of 0.0008 inch. It will be recognized by those skilled in the art that the wall thickness of the base layer balloon 302 may be increased or diminished as required.

The balloon base layer 302 may be omitted from a fiber-reinforced balloon 300, in accordance with one embodiment. Instead, a base layer 302 of a polymer may be applied to a removable mandrel 320 (FIG. 3b) and cured into the shape of a balloon. The mandrel 320 may be made from a variety of materials in the shape of the interior wall of the desired finished balloon. For example, a removable base balloon may be used as the mandrel 320. The mandrel 320 may be made of collapsible metal or polymeric bladder, foams, waxes, low-melting metal alloys, and the like. After the polymer is cured, the base layer 302 may be removed from mandrel 320 or the mandrel removed from the base layer by melting, dissolving, fracturing, compressing, pressurizing, or other suitable removal techniques.

Forming balloon 300 using mandrel 320 permits the use of alternative processing techniques can be employed which do not limit the parameters of temperature, force, and pressure, during the forming process. The materials used for the balloon construction are not limited to those that conform to the present art of forming a balloon with pressure, temperature, and force, such as, for example, those utilized for forming a balloon from a tube made from a polymeric material. Stronger fiber-reinforced balloons 300, with higher pressure and better damage resistance, can be formed with smaller geometries, in particular balloons having thinner walls. The resulting fiber-reinforced balloons 300 may be stronger, softer and more flexible.

Figure 4A:
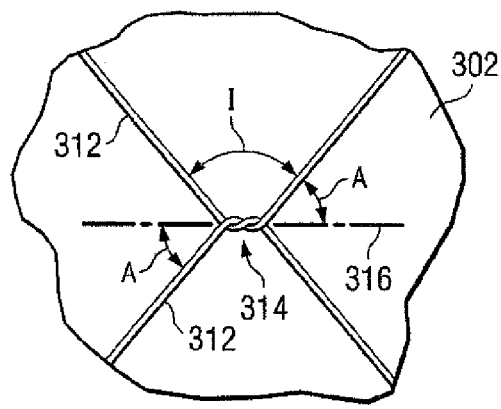
FIG. 4*a* is an enlarged portion of the medical balloon of FIG. 3.

Referring now to FIG. 4a, there is illustrated an enlarged portion of the medical balloon 300 showing how the individual fibers 312 may be laid over the surface of the base balloon 302 to make up the single braided fiber reinforcement layer 310. The fibers 312 are preferably formed of a substantially inelastic material. After placement on the balloon, each fiber 312 leading into, and out of a junction or intersection 314 with other fibers will form an angle (denoted "A") with the longitudinal axis 316 of the balloon. The braided fiber layer 310 is affixed to the outer surface of the base balloon 302 using an adhesive (not shown). In some embodiments, the braid angle "A" may vary from location to location over the surface of the balloon to provide the best fit for the braided layer. In preferred embodiments, however, the braid angle "A" at each particular location does not substantially change when the balloon goes from an uninflated state to an inflated state, or vice versa.

Depending upon the braiding pattern and style used, the fibers in the braided layer may be looped around each other one or more times at each intersection, or they may merely pass above or below one another at each intersection. Regardless, the fibers will form an angle with one another at each intersection.

In one variation, a single fiber 312 may extend continuously over the length of base balloon 302 between necks 308. In this variation, the fiber 312 changes direction at longitudinally spaced apart intervals corresponding to junctions 314 with interconnecting fibers while still extending continuously in a generally longitudinal direction over base balloon 302 between necks 308. Fiber 312 changes direction in that the interior angle (designated "I") between the fiber approaching the junction and the fiber extending away from the junction is less than one hundred and eighty degrees in the plane defined by the fiber. In this configuration, fibers 312 may extend longitudinally over base balloon 302 between necks 308 with substantially no fibers extending continuously completely around the circumference of the base balloon.

In another variation, a single fiber 312 may extend continuously around the circumference of base balloon 302. In this configuration, the fiber 312 changes direction at circumferentially spaced apart intervals corresponding to junctions 314 with interconnecting fibers while still extending in a generally circumferential direction around the circumference of base balloon 302. In the case of a substantially rectangular braid, the change in direction is approximately ninety degrees. In this variation, fibers 312 may extend continuously and circumferentially around base balloon 302 between necks 308 with no fibers extending continuously over the length of base balloon 302 between necks 308.

The fibers 312 of fiber layer 310 may be inelastic fiber, typically made of an inelastic fibrous material. An inelastic fiber is a fiber that has very minimal elasticity or stretch over a given range of balloon pressures, Some fibrous materials are generally classified as inelastic although the fibrous material may have a detectable, but minimal, elasticity or stretch at a given balloon pressure.

The fibers 312 of braided fiber layer 310 may be high-strength fibers, typically made of a high-strength fibrous material. Some high strength inelastic fibrous materials may include Kevlar, Vectran, Spectra, Dacron, Dyneema, Teflon (PBT), Zylon (PBO), Polyimide (PIM), other ultra high molecular weight polyethylene, aramids, polyesters nylons, and the like.

In one variation, fibers 312 are ribbon-shaped, where the width of the individual fiber is larger than the thickness of the fiber such that the fiber has a somewhat rectangular cross-section. Fibers 312 have a nominal thickness of about 0.003 inch and may be flattened on a roll mill or otherwise processed to achieve the ribbon shape. The dimensions of the flattened fibers may vary from about 0.0005 inch to about 0.003 inch or more, depending upon the particular material and application.

Referring now to FIGS. 4b and 4c, in other variations, the braided reinforcing layer is formed by first forming three or more tows, i.e., untwisted bundles of smaller continuous fibers or filaments, and then braiding the tows together. FIG. 4b shows a portion of a reinforcing layer 410 braided in an "over-1-under-1" diamond bi-axial pattern, and FIG. 4c shows a portion of another reinforcing layer 420 braided in an "over-2-under-2" regular hi-axial pattern. In the diamond braid pattern of FIG. 4b, a first plurality of tows or bundles of filaments 412 extend in a first direction, while a second plurality of tows 414 extend in a second direction. Each tow 412 travels over and under a single tow 414 at a time, while each tow 414 similarly travels over and under a single tow 412 at a time to form the diamond braid pattern. In FIG. 4c, two pluralities of tows are again used, a first plurality of tows 422 extending in a first direction, and a second plurality of tows 424 extending in a second direction. In this case, however, each tow 422 travels over and under two tows 424 at a time, while each tow 424 similarly travels over and under two tows 422 at a time to form the braid pattern. These examples are intended to be illustrative rather than limiting, as it will be appreciated that any other regular or fancy bi-axial or tri-axial braid pattern or other braid pattern known in the art can be used to form the braided reinforcing layer.

Regardless of the braiding pattern used for the braided reinforcement layer, each course, or row of fibers (or tows) will define a braid angle (denoted A1 and A2) with the longitudinal axis 316 of the balloon, and each intersection between fibers (or tows) will define an intersection angle (denoted B). Once the braided fiber reinforcement layer has been affixed in place on the balloon, these angles will remain substantially unchanged when the balloon goes from an uninflated state to an inflated state.

Referring now to FIGS. 4d and 4e, the fiber bundles or tows used in the braided reinforcing layers such as those shown in FIGS. 4b and 4c may have different cross sections. FIG. 4d shows a tow 430 comprising a plurality of individual fibers 432 bundled such that the tow has a generally circular cross-section, wherein the thickness (denoted t) of the tow is substantially the same as the width (denoted w). FIG. 4e shows another tow 440 comprising a plurality of fibers individual 442 bundled such that the tow has a generally flat or ribbon-like cross-section, wherein the thickness t of the tow is substantially smaller than the width w. It will be appreciated that in some cases all of the fibers in a particular tow may be the same size (e.g., diameter), same strength, and the same material, whereas in other cases fibers of different sizes, strengths and/or materials may be used in the same tow. Further, the braided reinforcing layer may be formed by braiding uniform tows, or by braiding tows having different characteristics.

Figure 5D:
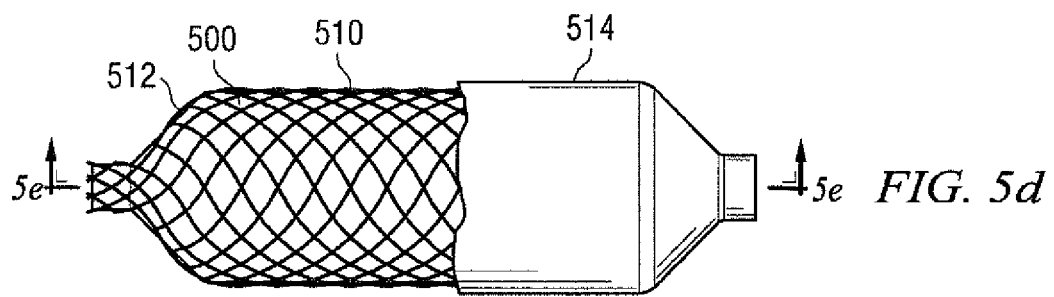

Referring now to FIGS. 5a-5f and 6, braided fiber reinforcement layer 310 may be applied to base balloon 302 using several methods. In one method, a free-standing braided fiber sleeve 510 formed from fibers 512 is prepared independently of the base balloon 502 (FIG. 5a). The braided sleeve 510 may be a seamless biaxial or triaxial tubular sleeve. Preferably, the sleeve 510 will have seamless fiber continuity from end to end. In one variation, each of fibers 512 extends continuously over base balloon 502 from end to end. Subsequently, the braided fiber sleeve 510 is pulled over the inflated balloon 502, expanding over the contours of the balloon (FIG. 5b). Base balloon 502 may be formed or positioned on a mandrel, similar to that illustrated in FIG. 3a prior to pulling braided fiber sleeve 510 over the base balloon 502.

Finally, the sleeve 510 is snugged down against the base balloon 502 using the "Chinese finger trap" effect to conform the sleeve to the dimensions of the base balloon and the excess sleeve material 520 is then cut off and discarded (FIG. 5c). The braided reinforcement 510 is typically impregnated with resin or adhesive such as a polyurethane after positioning, although in some embodiments, the fiber sleeve is impregnated prior to placement. The resin or adhesive coated fibers are consolidated with the base balloon 502 by curing to form the finished non-compliant braid-reinforced balloon 500. In the embodiment just described, the braided fabric layer 510 is the only reinforcing layer, but in other embodiments, the braided fabric layer may be used above, below, or between other reinforcing layers.

In another method (FIG. 6), the braided fiber reinforcement layer 610 is braided directly onto the base inflated balloon 602 using braiding equipment of known design. In this in situ method, the adhesive may be applied to base balloon 602 and/or to the reinforcing fibers prior to, during, or after the braiding process. By applying the fibers in situ, the greatest control may be obtained over the fiber density and angle at each part of the base balloon profile.

Figure 5E:
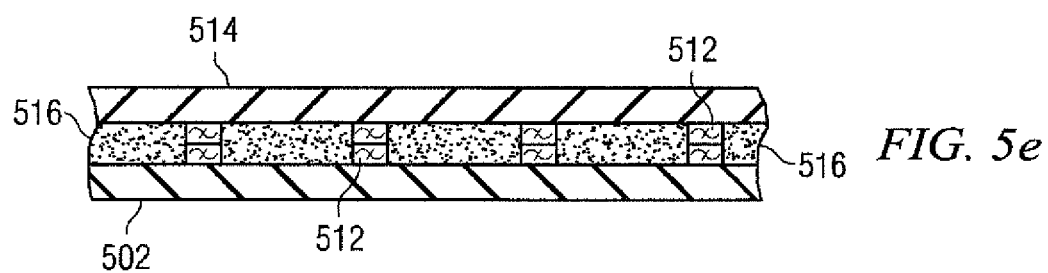
FIG. 5e is a partial sectional view of the medical balloon taken along line e-e of FIG. 5d.
Figure 5F:
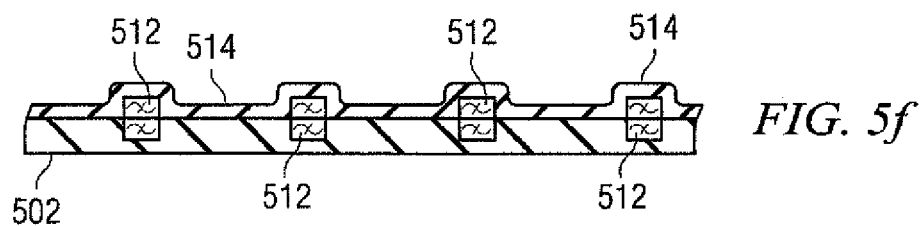
FIG. 5f is a partial sectional view illustrating an alternate construction of the medical balloon of FIG. 5d.
Figure 6:
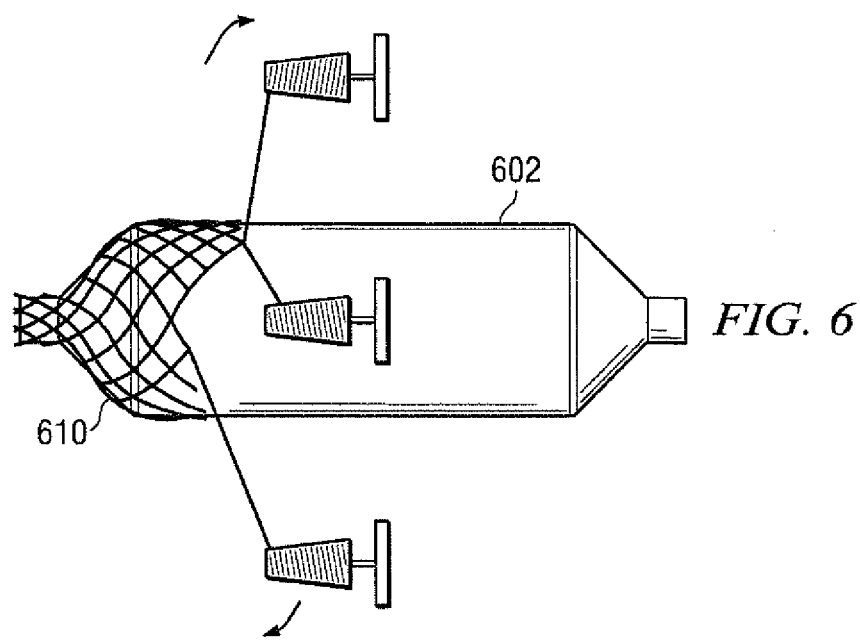
FIG. 6 shows a method of making a non-compliant medical balloon having a braided fiber reinforcement layer in accordance with yet another embodiment.

Referring to FIG. 5d, a polymer outer coating layer 514 may be applied over fiber reinforcement sleeve 510 as a film or by means of spray coating, dipping or other deposition process. The thickness of the polymeric outer coating layer 514 may be determined by the characteristics of the desired fiber-reinforced balloon 500. The polymeric solution used for the outer coating layer 514 may be formed from the same polymer as the polymer base balloon layer 502. The outer coating layer 514 may be made from a different polymer than the inflated polymeric balloon base layer 502. Where the polymers are different, the polymers may be chosen to be compatible to reduce or prevent separation of the composite balloon 500. As illustrated in FIG. 5e, outer layer 514 may be secured to base balloon 502 with an adhesive 516 with fibers 514 disposed between the outer layer and the base balloon. In one embodiment, adhesive 516 secures each fiber 512 substantially entirely along its length to base balloon 502 and/or to outer layer 514. Alternatively, as shown in FIG. 5f, outer layer 514 may be fused to base balloon 520 by means of solvent welding, heat, pressure or a combination thereof. In either case, fibers 514 are secured in position between the base balloon 502 and outer layer 514 such that the braid angle "A" (FIG. 3a) does not substantially change when the balloon goes from an uninflated state to an inflated state.

Polymers and copolymers that may be used as the outer coating layer 514 of the fiber/polymeric matrix include the conventional polymers and copolymers used in medical balloon construction. Typical suitable substances may include polyethylene, nylons, polyethylene terephthalate (PET), polycaprolactam, polyesters, polyethers, polyamides, polyurethanes, polyimides, ABS copolymers, polyester/polyether block copolymers, ionomer resins, liquid crystal polymers, and rigid rod polymers.

In one variation, the same or compatible polymer materials polymer materials are used to form base balloon 502 and outer coating layer 514. As illustrated in FIG. 5f, in this embodiment, rather than using a resin or adhesive to affix fiber layer 510 to base balloon 502, the base balloon and outer layer 514 are fused together by means of solvent welding, heat, pressure or a combination thereof. Welding base balloon 502 to outer coating layer 514 is believed to form a stronger connection between the base balloon and the outer coating. In one variation, fusing base balloon 502 to outer layer 514 secures each of fibers 512 substantially entirely along its length between the base balloon 502 and outer layer 514.

Figure 7A:
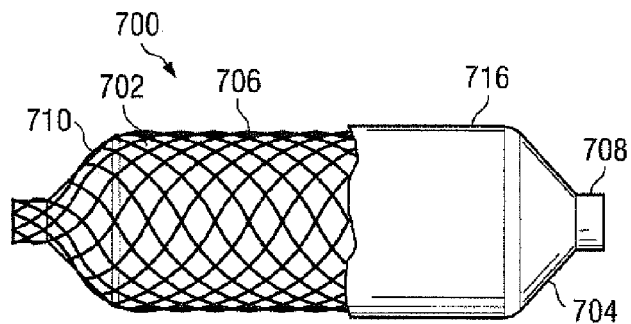
FIG. 7a is a side view of a non-compliant braid-reinforced medical balloon having a further over-coating layer.

Referring now to FIG. 7a, there is illustrated a non-compliant medical balloon 700 having braided fiber reinforcement 710 in accordance with another embodiment. Balloon 700 includes base balloon 702 having conical end portions 704 connected to a cylindrical center section 706 with reduced diameter necks 708 extending from the apex of each conical end portion 704, In this embodiment, a further overcoating layer 716, formed of a polyether block amide sold under the trademark Pebax® or similar thermoplastic material, may be pressure-molded over the braided fiber reinforcement layer 710 to further hold it in place or to provide an abrasion resistant coating to the balloon.

Figure 7B:
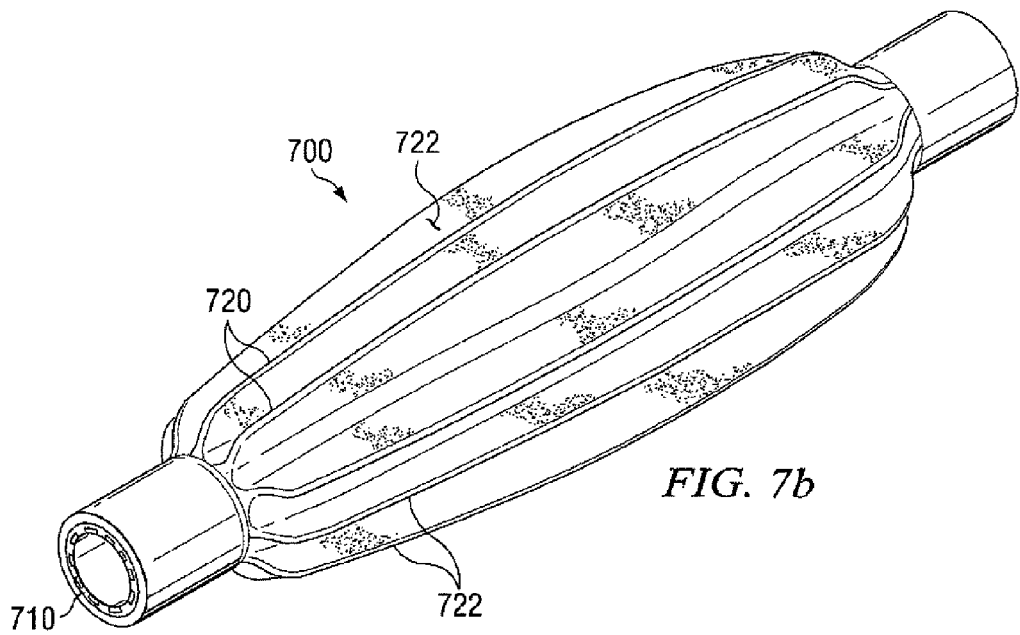
FIG. 7b is a perspective view of the non-compliant braid reinforced balloon of FIG. 7 in the collapsed or deflated state.

FIG. 7b shows the non-compliant medical balloon 700 in the deflated or collapsed state. Folds 720 in outer surface 722 decrease the diameter of the medical balloon 700 for insertion by means of a catheter or similar device. The "leaves" of each fold may then be rolled circumferentially about the interior catheter (not shown) within the balloon to form a compact package. As the deflated medical balloon 700 inflates, the balloon folds 720 substantially disappear until the balloon reaches an inflated size as shown in FIG. 7a. Since medical balloon 700 is non-compliant, once the balloon is fully inflated, it has a length and diameter that do not change as the pressure on the interior of the balloon increases.

Regardless of the method for applying and affixing the braided fiber reinforcing fibers to the base balloon, after the fibers are adhesively affixed in place, then the angle and location of the braids will not change between the inflated state and the deflated state of the balloon. Thus, following manufacture, the now composite reinforced balloon may be folded up and rolled to form a small cross-section as with the prior art. When later re-inflated in the body, the braided fiber reinforcing will maintain its position and spacing along the conical ends and center sections of the balloon to prevent pressure-related failures. If the balloon has been subsequently coated with Pebax®, or another over-coating material, then the balloon will also exhibit superior abrasion-resistant qualities as well.

Figure 8:
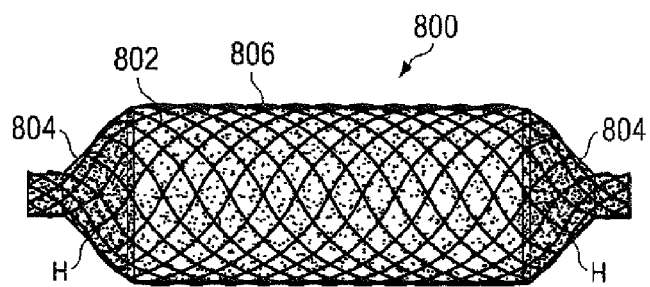
FIG. 8 shows a non-compliant braid-reinforced medical balloon having different strength adhesives used at different portions of the balloon.

Referring now to FIG. 8, in yet another embodiment, different strength adhesives are used at different portions of the balloon 800 to affix the braided fiber reinforcing layer 810 to the base balloon 802. It will be appreciated that, in most cases, the higher the strength of an adhesive, the lower its flexibility. Since a major location of failures in medical balloons occurs in the conical end sections 804, in this embodiment, a high-strength adhesive (denoted by shaded area "H") is used to affix the reinforcing fibers 810 to the base balloon 802 at these conical end sections. This prevents the fibers 810 from moving during inflation and causing a weak point in the balloon. The remaining generally cylindrical center section 806 of the balloon may have the fibers 810 adhered using ordinary strength adhesives having improved flexibility. For example, a high viscosity urethane adhesive may be used to secure fiber reinforcement layer 810 to conical end section 804 while a lower viscosity urethane adhesive may be used to secure layer 810 to cylindrical center section 806. Thus, the non-compliant balloon 800 exhibits increased burst strength with a minimum reduction in the overall flexibility of the device.

Figure 9A:
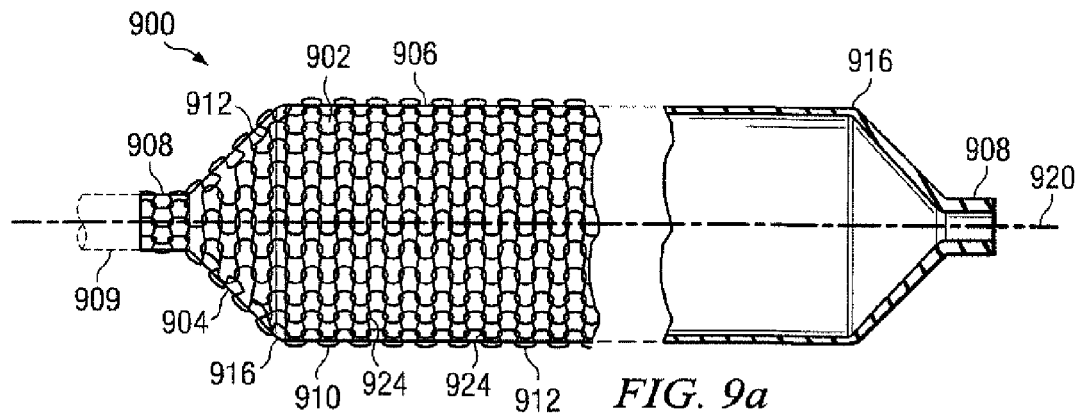
FIG. 9a is a partial cross-sectional side view of a non-compliant medical balloon having knitted fiber reinforcement in accordance with one embodiment of the disclosure.
Figure 9B:
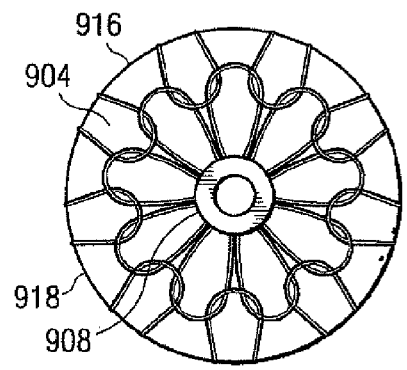
FIG. 9b is an end view of the non-compliant medical balloon of FIG. 9.
Figure 10:
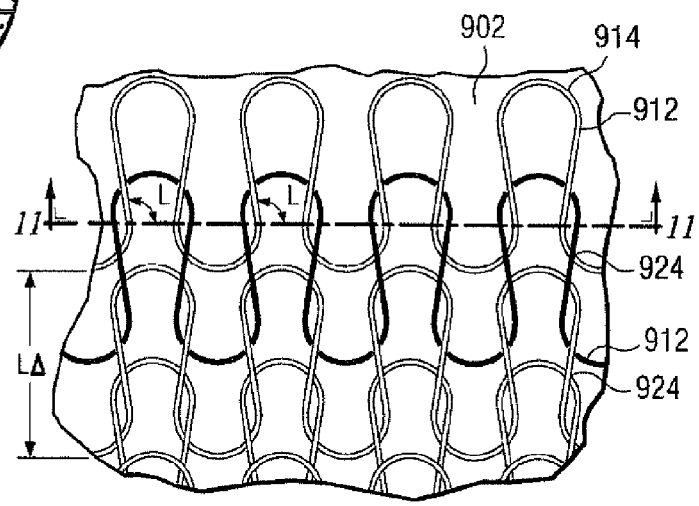
FIG. 10 is an enlarged portion of the medical balloon of FIG. 9.

Referring now to FIGS. 9a, 9b, and 10, a non-compliant medical balloon 900 having a knitted fiber reinforcement layer 910 may include a base balloon 902 having pairs of conical end sections 904 and a relatively cylindrical center section 906 located therebetween. A shoulder 916 is formed at the junctures of each of conical end sections 904 and cylindrical center section 906. Shoulders 916 each define a circle 918 circumscribing the perimeter of the juncture of cylindrical center section 906 and conical end sections 904.

A small-diameter cylindrical neck 908 may extend outwardly from each end section 904 for attachment to a catheter 909 (shown in phantom). The base balloon 902 may be formed of a thin film polymer material using a blow-molding process, resulting in the wall thickness of the end sections tapering considerably from relatively thick at the neck 908 to relatively thin at the center section 906.

In the illustrated embodiment, the fiber reinforcement comprises a single layer 910 of knitted fibers 912 that is attached to the base balloon 902 when in its inflated configuration. The knitted fiber reinforcement layer 910 may include rows of loops 914, each of which is pulled through the loops of the row below it. In this manner fibers 912 are mechanically interlocked by passing over or under an interconnected fiber at junctions 924. In one variation, fibers 912 change directions at each junction 924, while still extending in a generally longitudinal or circumferential direction.

In one variation, knitted fiber reinforcement layer 910 may comprise a seamless tube and in other variations, it may be constructed from a flat knitted reinforcement fabric having one or more seams. In one embodiment, layer 910 comprises a seamless tube extending continuously from end-to-end of base balloon 902. In one variation, each of fibers 912 extend across shoulder 916 at an angle of less than ninety degrees relative to longitudinal central axis 920 of base balloon 902 and at an angle relative to the plane defined by circle 918 such that longitudinal and transverse components of forces applied to base balloon 902 upon inflation are transmitted across shoulder 916 by fibers 912.

As illustrated, the knitted fiber reinforcement layer 910 has a very high "porosity," i.e., a relatively large amount of open space between braid fibers 912. It will be appreciated, however, that other knit forms having different patterns and porosities may be used in other embodiments. It will also be appreciated that different knit configurations may be used for the knitted fiber reinforcement layer 910, including weft, warp, circular, flat and custom knit forms. The knit density of fiber reinforcement layer 910 will be similar to the braid density of braided fiber reinforcement layer 310 in FIG. 3a.

Non-compliant medical balloon 900 including base balloon 902 and knitted fiber layer 910 may be constructed of the same materials in generally the same manner as balloon 300 of FIG. 3a, except that fiber reinforcement layer 910 is knitted instead of braided. Knitted fiber layer 910 may be installed on base balloon 902 in substantially the same fashion as described in connection with FIGS. 5A-5C above or, alternatively, knitted in place on base balloon 902. The knitted fabric reinforcing layer may be the only reinforcing layer, or it may be affixed above, below, or between other reinforcing layers.

Figure 3B:
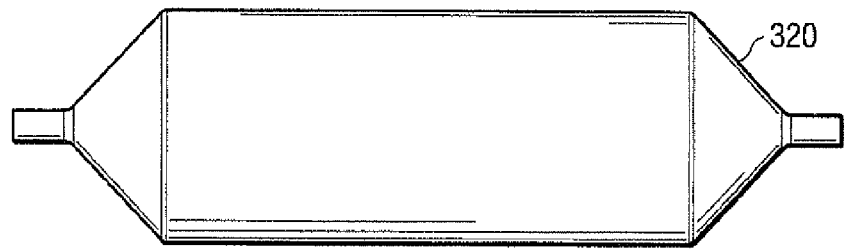
FIG. 3*b* is a side view of a mandrel suitable for use in forming a base component of the medical balloon of FIG. 3.

Base balloon 902 may be formed from a variety of polymers and copolymers. For example base balloon 902 may be formed from polyethylene terephthalate, (PET), polycaprolactam, polyesters, polyethers, polyamides, polyurethanes, polyimides, ABS, nylons, copolymers, polyester/polyether block copolymers, ionomer resins, liquid crystal polymers, rigid rod polymers and other polymers used for medical balloons. In one embodiment, base layer balloon 902 be blow-molded balloon from oriented polyethylene terephthalate (PET). Base balloon 902 may also be formed by applying a polymer solution to a mandrel such as illustrated in FIG. 3b and curing the solution.

Figure 11:
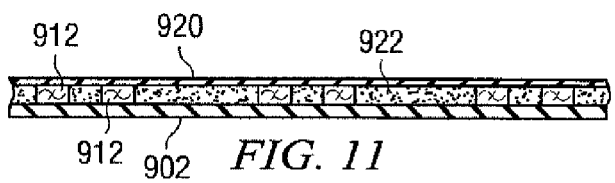
FIG. 11 is a partial sectional view of the medical balloon of FIG. 9 taken along line 11-11 of FIG. 10.
Figure 12:
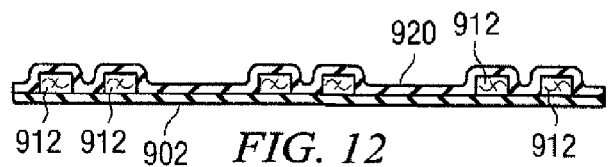
FIG. 12 is a partial sectional view of an alternate construction of the medical balloon of FIG. 10.

Turning to FIGS. 10-12, an enlarged portion of the medical balloon 900 illustrates the general configuration of individual fibers 912 as laid over the surface of the base balloon 902 to form knitted fiber reinforcement layer 910. In one configuration, knitted fiber reinforcement layer is 910 stretched taut, e.g., to the point that further force will not extend the layer, before the layer is secured to base balloon 902. Fibers 912 are preferably formed of a high-strength substantially inelastic material. Such fibers may include Kevlar, Vectran, Spectra, Dacron, Dyneema, Teflon (PBT), Zylon (PBO), Polyimide (PIM), other ultra high molecular weight polyethylene, aramids, polyesters nylons, and similar materials. When secured on base balloon 902, each loop 914 will have a loop length (denoted "LD"). In one embodiment, the loop lengths LD of loops 914 will not change substantially when the balloon is inflated or deflated.

In some embodiments, a single fiber 912 forms multiple spaced apart loops 914 extending continuously over the length of fiber reinforcement layer 910. In this configuration, fiber 912 will extend continuously, in a generally longitudinal direction, between necks 908 of base balloon 902, while changing directions with each loop. In this variation, fiber 912 may extend continuously in a generally longitudinal direction over base balloon 902 between necks 908 without passing around the circumference of the base balloon. In one configuration, all of fibers 912 may extend generally longitudinally along the length of base balloon 902 between necks 908 with substantially no fibers extending completely around the circumference of base balloon 902 anywhere between necks 908.

In another variation, a single fiber 912 forms multiple spaced apart loops extending continuously around the circumference of fiber reinforcement layer 910. In this configuration, fiber 912 will extend a generally circumferential direction around the circumference of base balloon 902 while changing directions with each loop. In this variation, fiber 912 may extend continuously in a generally circumferential direction around base balloon 902 between necks 908 without extending longitudinally over the length of base balloon 902 between necks 908. In one configuration, all of fibers 912 may extend generally continuously and circumferentially around the circumference of base balloon 902 with substantially no fibers extending longitudinally over the entire length of base balloon 902 between necks 908.

After placement on the balloon, each fiber 912 leading into, and out of, a loop 914 with other fibers will form an angle (denoted "L") with a longitudinal axis 11-11 of the balloon. In some embodiments, the knit angle "L" may vary from location to location over the surface of the balloon to provide the best fit for the knitted layer. The knitted fiber layer 910 is secured to the outer surface of the base balloon 902 using an adhesive such as a polyurethane and/or overcoated with a material such as Pebax®.

In other embodiments, as illustrated in FIG. 11, fibers 912 are disposed between an outer layer 920 and base balloon 902 with an adhesive layer 922 securing the outer layer, fibers and base balloon together. As shown in FIG. 12, in yet other variations outer layer 920 may be fused to base balloon 902 by means of solvent welding, heat, pressure or a combination thereof with fibers 912 are disposed between outer layer 920 and base balloon 902 such that the base balloon, fibers and outer layer are secured together and affixed in position relative to each other.

In preferred embodiments, the knit angle "L" at each particular location does not substantially change when the balloon goes from an uninflated state to an inflated state, or vice versa. Similarly, in the same or other preferred embodiments, the loop length "LD" does not substantially change when the balloon goes from an uninflated state to an inflated state, or vice versa. In other words, the spacing of loops 914 relative to adjacent connected loops 914 and base balloon 902 does not change when the balloon is inflated.

It will be appreciated by those skilled in the art having the benefit of this disclosure that the disclosure provides a non-compliant medical balloon having braided reinforcement and methods relating to the fabrication and/or use of same. It should be understood that the drawings and detailed description herein are to be regarded in an illustrative rather than a restrictive manner, and are not intended to limit the flowing claims to the particular forms and examples disclosed. On the contrary, further modifications, changes, rearrangements, substitutions, alternatives, design choices, and embodiments apparent to those of ordinary skill in the art, without departing from the spirit and scope of the disclosure and following claims. Thus, it is intended that the following claims be interpreted to embrace all such further modifications, changes, rearrangements, substitutions, alternatives, design choices, and embodiments.

What is claimed is:

1. A non-compliant medical balloon comprising:
   a base balloon having a longitudinal axis, said balloon including a first section with a first diameter and a second section with a second diameter; and
   a reinforcement layer comprising a plurality of braided fibers, wherein the braided fibers form a braid angle with respect to one another, and wherein the braid angle at a first location of the reinforcement layer is less than the braid angle at a second location of the reinforcement layer;
   wherein there is substantially no change in the braid angles when the balloon changes from a deflated state to an inflated state.

2. The medical balloon of claim 1, further including a pair of spaced-apart, generally conical end section and a generally cylindrical section therebetween, wherein the braid angle in at least one of the conical end sections is less than the braid angle in the center section.

3. The medical balloon of claim 1, wherein the plurality of braided fibers extend in a substantially longitudinal direction over the base balloon, and wherein no single fiber extends completely around the circumference of the base balloon.

4. The medical balloon of claim 1, wherein the plurality of braided fibers extend in a substantially circumferential direction over the base balloon, and wherein no single fiber extends completely over the length of the base balloon.

5. The medical balloon of claim 1, further including an outer coating layer.

6. The medical balloon of claim 1, further including an adhesive layer.

7. The medical balloon of claim 1, wherein the reinforcement layer comprises a fabric including braided fibers at a density of 20-60 pics per inch.

* * * * *